United States Patent
Cully et al.

(10) Patent No.: US 6,702,845 B1
(45) Date of Patent: Mar. 9, 2004

(54) COMPACTED IMPLANTABLE MEDICAL DEVICES AND METHOD OF COMPACTING SUCH DEVICES

(75) Inventors: Edward H. Cully, Flagstaff, AZ (US); Keith M. Flury, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/346,822

(22) Filed: Jan. 17, 2003

(51) Int. Cl.[7] .............................................. B21D 39/00
(52) U.S. Cl. ........................... 623/1.15; 29/517; 29/282
(58) Field of Search ............................ 623/1.2, 1.23, 623/1.12, 1.15

(56) References Cited

U.S. PATENT DOCUMENTS

| | | | |
|---|---|---|---|
| 5,546,646 A | * 8/1996 | Williams et al. | 29/407.08 |
| 5,662,713 A | * 9/1997 | Andersen et al. | 623/12 |
| 5,873,906 A | 2/1999 | Lau et al. | 623/1 |
| 5,911,452 A | * 6/1999 | Yan | 29/516 |
| 5,919,225 A | 7/1999 | Lau et al. | 623/1 |
| 5,920,975 A | 7/1999 | Morales | 29/282 |
| 5,928,258 A | 7/1999 | Khan et al. | 606/191 |
| 5,931,851 A | * 8/1999 | Morales | 606/194 |
| 6,063,092 A | * 5/2000 | Shin | 606/108 |
| 6,082,990 A | * 7/2000 | Jackson et al. | 425/517 |
| 6,092,273 A | * 7/2000 | Villareal | 29/516 |
| 6,096,027 A | 8/2000 | Layne | 606/1 |
| 6,132,458 A | * 10/2000 | Staehle et al. | 623/1.11 |
| 6,224,627 B1 | 5/2001 | Armstrong et al. | 623/1.23 |
| 6,309,383 B1 | 10/2001 | Campbell et al. | 606/1 |
| 6,352,561 B1 | 3/2002 | Leopold et al. | 623/123 |
| 6,510,722 B1 | * 1/2003 | Ching et al. | 72/402 |
| 2002/0138129 A1 | * 9/2002 | Armstrong et al. | 623/1.11 |

FOREIGN PATENT DOCUMENTS

| | | |
|---|---|---|
| EP | 630623 | 12/1994 |
| EP | 903122 | 3/1999 |
| WO | 00/42948 | 7/2000 |

* cited by examiner

*Primary Examiner*—Corrine McDermott
*Assistant Examiner*—Thomas J Sweet
(74) *Attorney, Agent, or Firm*—David J. Johns (57) ABSTRACT

An expandable implantable device is provided having a very small introductory profile. The small introductory profile is achieved by de-coupling the forces necessary to initially constrain the expandable device from the forces necessary to achieve full compaction of the device. As a result, the device can be made from more delicate materials that do not have to withstand overly aggressive compaction forces in order to achieve a fully compacted introductory profile.

16 Claims, 11 Drawing Sheets

COMPACTED IMPLANTABLE MEDICAL DEVICES AND METHOD OF COMPACTING SUCH DEVICES

BACKGROUND OF THE INVENTION

1. Field of the Invention

The present invention relates to medical devices that are delivered into patients by catheters using minimally invasive procedures and methods of compacting such devices.

2. Description of Related Art

Arteriosclerosis affects a significant portion of the population. The progressive nature of the disease can result in severe vessel stenosis (narrowing) and ischemic conditions distal to the stenosis. Although conventional surgical interventions have proven highly effective at treating such conditions, in many cases associated procedural morbidity and mortality has driven the development of alternate "minimally invasive" therapies. These therapies are particularly useful when a lesion to be treated is deep within the body, such as in aortic and cardiac vessels or within the skull base (such as, a carotid artery or deep neuro-vasculature). These minimally invasive techniques have enjoyed increasing success and acceptance in the treatment of several vascular diseases including aneurysmal and occlusive disease.

In a typical minimally invasive procedure, upon gaining percutaneous access to the patient's vascular system, a guidewire is introduced and guided under fluoroscopic visualization to the intended site of therapy. The guidewire then serves as "rail" onto which other subsequent devices are guided through the vessels to the site. A typical occlusive lesion may require pre-dilation (e.g., PTA or PTCA) and the placement of an endovascular device (such as a stent or stent-graft). This device may then permanently reside within the lumen of the vessel. All components for these procedures are delivered within the vessel (i.e., "endoluminally") and actuated remotely from outside of the body. Since open surgery is not required, these procedures are considered "minimally invasive."

For the purposes of the following description, endovascular devices may be classified in two general categories: (1) plastically deformable (e.g., balloon expandable); and (2) self-expanding.

Plastically deformable devices are generally deployed by deforming the device at the site of therapy, usually by internal pressure such as inflation of an angioplasty balloon. Devices of this type are generally made of a ductile bio-acceptable material that provides little recoil after dilation. A major advantage of the plastically deformable device is obviating the need for incorporating a restraining device into the delivery system since balloon inflation is all that is needed for proper deployment.

Self-expanding devices, in contrast, are designed to spontaneously deploy in situ once they are released from a constrained profile. They are generally made from some type of elastic, super-elastic, and/or shape memory metal or polymer. Advantages of this type of device are: 1) self-deployment obviates the need for high pressure ballooning at the therapy site; 2) clinical application of self-expanding devices has demonstrated a significant increase in minimum lumen diameter as compared to balloon expandable devices; and 3) super-elastic, pseudo-elastic, and shape memory alloys provide a high degree of compliance and will maintain their expanded profiles despite subsequent mechanical deformation (such as forces that might be encountered in an accident or other pressure applied through a patient's skin).

Both device categories share a common requirement that they must be introduced to the body from an access site remote to the actual therapy site. As a result, they must be inserted in a first small "introductory" configuration, guided at this introductory profile through a patient's vasculature, and deployed through an actuation mechanism to achieve a second "functional" configuration.

Many techniques have been developed to configure endovascular devices at a small introductory profile in preparation for insertion to the body. These techniques vary depending upon the category of the individual device.

In the instance of plastically deformable devices, the device may only need to be mechanically crimped onto a balloon prior to insertion to the body. Since this device is made of substantially non-recoiling material, the device, once crimped onto the balloon, will be readily retained on the balloon while being guided to the lesion site.

Although crimping may be done by hand, manual techniques are often unsatisfactory due to non-uniform pressure applied to the crimped device. This can lead to non-uniform device expansion and increased variability in clinical performance. As a result, a number of devices and processes have been developed to reliably and consistently crimp plastically deformable devices onto, or into, a delivery system.

U.S. Pat. No. 5,920,975 to Morales describes a tool that winds a spring-like element around a plastically deformable device while it is mounted upon a delivery balloon. As the spring is tightened, pressure is applied to the device intending to crimp it onto the balloon.

EP Patent Application 630,623 to Williams et al. describes two methods to reduce the cross section of a device. In one embodiment, a plastically deformable device is mounted upon a delivery balloon and placed between reciprocating flat plates. The flat plates act to roll the device while reducing its cross sectional profile. The additions of force and size gauges, as well as inherent consistency of the machine, make this an improvement over the manual crimping technique of rolling the device between fingers.

In another embodiment of Williams et al., a plastically deformable device is mounted on a delivery balloon and then inserted into a chamber. This chamber is lined with a sealed, distensible bladder that, upon inflation, applies a circumferential crushing force to the device. This crushing force is intended to reduce the device profile and securely mount the device on the balloon.

U.S. Pat. No. 6,309,383 to Campbell et al. describes a crimping tool that resembles a hand-held nutcracker or set of pliers. A plastically deformable device is mounted on a delivery balloon and inserted into an orifice in the apparatus. The crimping tool is squeezed to apply pressure to the outside of the device to radially compact the device onto the balloon.

EP Patent Application 903,122 to Morales describes a crimping tool that uses a set of jaws to radially constrict a plastically deformable device onto a delivery balloon. The segmented jaws are hinged on one end to allow them to open and accept a device and its balloon delivery system. Once the device is inside, a collar is slid over the outer surface of the jaws. Pressure applied against the jaws by the collar causes them to close, thereby crushing the device onto the balloon.

In the instance of self-expanding devices, the diametrical size of the device needs to be reduced to an "introductory" profile and held in place by some constraint. This is generally a more complex procedure than compacting a plastically deformable device since a steady constraint must be applied to the compacted device from its initial compaction to its ultimate deployment. This is typically accomplished using a tool or machine to reduce the device profile, and then the device is transferred in its compacted state to a restraining sheath, catheter, or other constraining means. The constraining means is kept actively engaged up to the time of deployment at the treatment site.

U.S. Pat. No. 6,096,027 to Layne describes an apparatus for crushing and loading a self-expanding device. This device utilizes a bag surrounding the device that is pulled through a tapered die (funnel). As the device moves through the funnel its cross sectional profile is reduced. Upon exiting the die, the bag is removed and the device is captured in a restraining tube or sheath.

U.S. Pat. No. 5,928,258 to Kahn et al. describes an apparatus for crushing and loading a self-expanding device that utilizes a cylindrical cartridge for receiving the device and another implement for transferring the device into a delivery sheath. The device is pulled into the first cartridge, and then a plunger mechanism is used to transfer it to an awaiting delivery sheath or catheter.

U.S. Pat. No. 5,873,906 to Lau et al. describes a method of "folding" a self-expanding device which entails flattening and rolling the device into a "jelly roll" configuration. The device is then restrained in this "introductory" profile through the use of a fiber based constraining mechanism, and applied to a delivery system. A series of fibers are likewise used to constrain a self-expanding device in U.S. Pat. No. 6,224,627 to Armstrong et al.

Further improvements in compacting self-expanding devices to a minimal introductory profile are disclosed in International Publication No. WO 00/42948 to Vonesh et al., which describes unique fluted funnel designs that allow self-expanding devices to be simultaneously folded and compacted through a funnel to a very low introductory profile.

While all of these prior devices may work well for their intended purposes, it is believed that further significant reductions in introductory profiles may still be possible. Two competing design parameters confront an implantable device designer in maximizing compaction of a device. In addition to having sufficient structural integrity to work for its intended purpose, a compacted implantable device design must balance: (1) the need to limit the amount of material comprising the implantable device so as to have less material to compact; and (2) the need to have a fairly robust implantable device that can withstand the considerable forces encountered in achieving extremely compact dimensions. While a device formed from thinner materials has less material to compact, such a device may not withstand the forces required to reach the smallest possible compacted state. In contrast, a robust implantable device that can be withstand aggressive "mashing" to smaller dimensions generally has too much material to achieve a small enough profile. This conflict between minimizing device bulk while maximizing device robustness is most clearly confronted when compacting a self-expanding implantable device through a funnel.

It is believed that the most effective means currently known for compacting a self-expanding device is to pull the device down to a compact size through one or more funnel devices, and particularly through a fluted funnel device. This process is very effective at achieving a small compacted size while imparting minimal damage to the implantable device. Unfortunately, the process of pulling a device through a funnel is limited by the robustness of the implantable device. In order to compact a device in a funnel, the device is attached to tether lines or similar means and then actuated through the funnel. This applies a number of forces to the implantable device, including the force necessary to compact the device as well as the friction forces applied by the funnel and any subsequent restraining means as the device is squeezed through these apparatuses. A thin, lightweight device has the advantage of having minimum material to compact, but such devices tend to pull apart as they are pulled through tight funnels to very small compacted dimensions. More robust devices that can withstand such extreme pulling forces can be provided, but these devices are by necessity bulkier and therefore limited in their ultimate compactability.

It is accordingly a purpose of the present invention to provide an improved method for compacting an implantable device that can achieve a highly compacted introductory profile.

It is a further purpose of the present invention to provide such a method for compacting that does not damage the device in the process of compaction and without the need to have an overly bulky implantable device.

It is still a further purpose of the present invention to provide an implantable device that has a very low delivery profile that is smaller than a profile that can be achieved by pulling the device through a funnel.

These and other purposes of the present invention will become evident from review of the following description.

SUMMARY OF THE INVENTION

The present invention provides unique implantable devices that have extremely small introductory profiles, and particularly interventional devices, and methods for achieving such small introductory profiles. The small profiles achieved with the present invention are possible by "decoupling" the forces required to pull an implantable device through a funnel into a retaining device from the forces required to compact the device fully to its introductory profile. For example, forces can be decoupled in the present invention by pulling an implantable device from a fully enlarged profile through a funnel and into a capture tube at an intermediate device profile. The intermediate profile should be one that limits the compaction and friction forces required to compact and capture the device to less than the longitudinal strength of the device. Once placed in the capture tube at the intermediate profile, the capture tube and device are then compressed further to a final delivery profile by swaging the capture tube.

The process of the present invention protects the integrity of the implantable device without requiring the implantable device to be more "robust" in order to withstand the cumulative compaction and friction forces of transforming it from its fully enlarged profile to its fully compacted profile.

In one embodiment the present invention comprises a method of reducing the cross sectional dimension of a medical device by providing a medical device having an initial cross sectional profile and a restraining member adapted to receive the medical device at a reduced profile. The profile of the medical device is first reduced, such as using a funnel or similar reduction device, to an intermediate cross sectional profile and then placed at this intermediate profile into the restraining member. Radial compressive force is then applied to the restraining member to further reduce the cross sectional profile of the medical device to a fully compacted profile suitable for delivery into a patient.

The present invention further provides a self-expanding stent with an extremely small introductory profile. The stent is one having a longitudinal tensile strength, an enlarged diameter, and a compacted diameter. Since it is created through the de-coupling process of the present invention, the compacted diameter of said stent is smaller than a diameter that could be obtained using a funnel alone to reduce the stent from its enlarged diameter to its compacted diameter.

DESCRIPTION OF THE DRAWINGS

The operation of the present invention should become apparent from the following description when considered in conjunction with the accompanying drawings, in which.

DETAILED DESCRIPTION OF THE INVENTION

The present invention provides an improved method for compacting an implantable device to a very small introductory profile, and low-profile devices created through such method.

As the terms "interventional" or "minimally invasive" devices or procedures are used herein they are intended to encompass any device or procedure whereby a medical treatment implement is delivered to a treatment site by use of wires and/or tubes threaded through vessels or other body passageways accessed remotely. Minimally invasive implantable devices encompassed by the present invention may include those employed in: balloon angioplasty; thrombectomy; stent, graft, or stent-graft placement; embolic filter device placement; remote diagnostic procedures, such as those employing fiber optic cameras, ultrasound monitoring, MRI monitoring, x-ray monitoring, etc.; remote therapeutic procedures, such as those employing cutting blades, lasers, heat application, cold application, radiation, drug delivery, etc.; and any other similar devices or procedures now known or later developed. Currently such interventional procedures are employed in large and small blood vessels, in other vessels in the body, such as in the bile duct, as well as in the respiratory, digestive, reproductive, and other body systems. As the term "patient" is used herein it is intended to encompass both humans and animals.

The present invention achieves an extremely small introductory profile for implantable devices by partially "decoupling" the forces required to pull an implantable device through a funnel into a capture tube from the forces required to compact the device fully to its introductory profile. In its simplest form, the forces are decoupled by pulling an implantable device from a fully enlarged profile through a funnel and into a capture tube at an intermediate device profile. The immediate profile is chosen so that the compaction and friction forces required to compact the device and place it in the capture tube are less than the longitudinal strength of the device. In this manner the combined forces required to place the device into the capture tube are less than the longitudinal strength of the device so as to avoid any device damage in the initial pull down step. Once placed in the capture tube at the intermediate profile, the capture tube and device are then compressed down to a final delivery profile by swaging the capture tube. Far greater compaction is possible using this process without applying any excessive longitudinal strain on the implantable device.

Overall, this process separates into multiple steps the forces required to achieve full compaction. The process protects the integrity of the implantable device without requiring the implantable device to be more "robust" in order to withstand the cumulative compaction and friction forces of transforming it from its fully enlarged profile to its fully compacted profile. In fact, the present invention can provide an implantable device at an introductory profile that it physically cannot achieve through compaction through a funnel alone.

Further decoupling of forces in the present invention can be provided by using a capture tube having one or more break zones therein. The capture tube can be split along the break zones into discrete capture tube segments that can each be separately removed from the device. Frictional forces applied to the implantable device during capture tube removal can thus be further reduced.

Referring now to the drawings, FIGS. 1 through 11 illustrate process steps of practicing one embodiment of the present invention, compacting an implantable device 30 from a fully enlarged deployed profile 32 to a fully compacted introductory profile 34. The term "profile" as it is used herein it is intended to encompass the overall general dimensions of an implantable device as viewed in cross section. "Profile" in the context of the present invention refers to the diameter of a device with circular cross-section as well as dimensions of implantable devices having oblong, triangular, rectangular, or other regular or irregular cross-sectional shapes.

Figure 1:
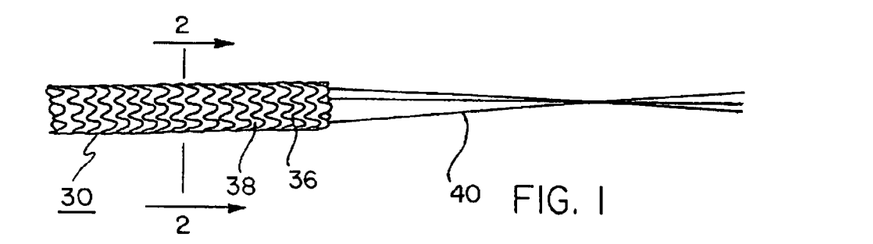
FIG. 1 is a side view of an implantable device, in this instance a stent-graft, prepared for compaction in accordance with the present invention, tether lines having been applied to the device.
Figure 2:
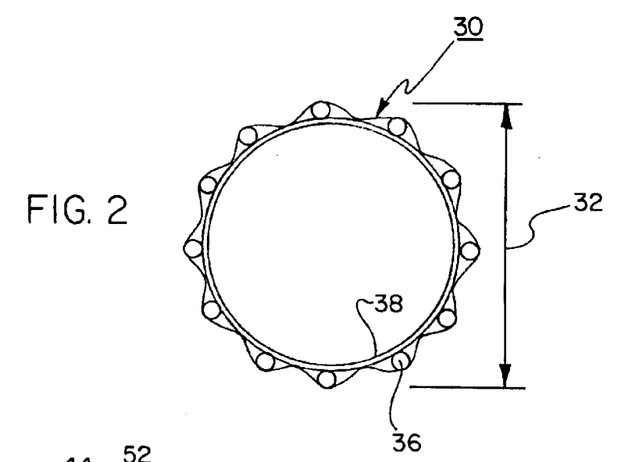
FIG. 2 is a cross-section view of the implantable device along line 2—2 of FIG. 1 at an initial enlarged cross-sectional dimension.

FIGS. 1 and 2 show an implantable device 30 of the present invention. In this instance, the implantable device comprises an implantable endoprosthesis having a stent 36 and a graft 38 component attached together. Endoprostheses of similar forms are commercially available from a number of sources. The endoprosthesis shown is illustrative of a variety of forms available from W.L. Gore & Associates, Inc., such as the VIABAHN™ tracheal endoprosthesis and the HEMOBAHN™ peripheral vascular endoprosthesis.

Figure 3:
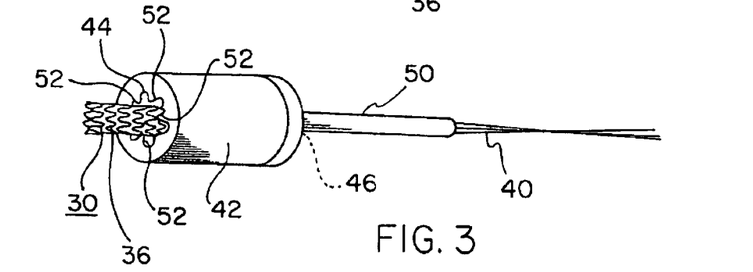
FIG. 3 is an isometric view of the device of FIG. 1 being pulled through a funnel into a capture tube having an inner diameter (ID) approximately equal to an intermediate cross sectional dimension.
Figure 4:
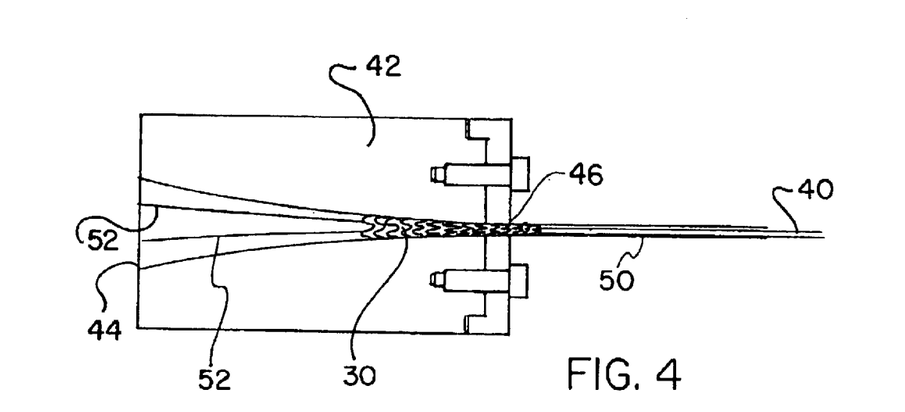
FIG. 4 is a cross-section view of the funnel, device, and capture tube of FIG. 3, with the device having been predominately compacted into the capture tube.
Figure 5:
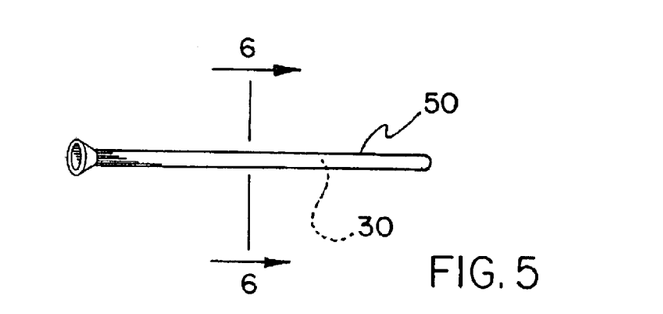
FIG. 5 is an isometric view of the capture tube having the implantable device contained therein.
Figure 6:
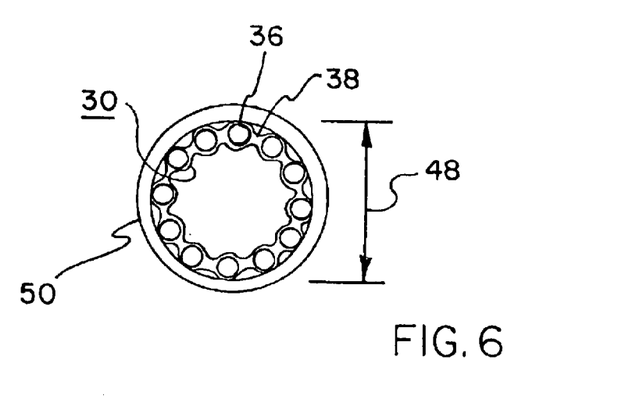
FIG. 6 is a cross-section view of the capture tube and device along line 6—6 of FIG. 5, showing the device at its intermediate cross sectional dimension.

In order to compact this device through a funnel, tether lines 40 can be attached to one end of the implantable device 30, as is shown in FIG. 1. As is shown in FIGS. 3 and 4, a funnel 42 is provided that has a wide opening 44 at one end approximately equal to the fully enlarged profile 32 and a narrow opening 46 at an opposite end approximately equal to an intermediate device profile 48. A restraining member or capture tube 50 is aligned with the narrow opening 46. The tether lines 40 are threaded through the funnel 42 and the capture tube 50 and the implantable device 30 is then pulled down into the capture tube, as is shown in FIGS. 3 and 4. Once the implantable device 30 is fully pulled within the capture tube, the tether lines 40 can be removed. FIGS. 5 and 6 illustrate the implantable device 30 fully indwelling within the capture tube 50 at the intermediate profile 48.

A preferred funnel 42 for use with the present invention has one or more longitudinal ribs or "flutes" 52 provided therein. Such flutes 52 can aid in the folding and compacting of the stent 36 elements as the device 30 is pulled through the funnel, as is taught in International Publication No. WO 00/42948 to Vonesh et al. (based on PCT Application PCT/US00/01557), incorporated by reference. It has been found that the orderly folding of the endoprosthesis during compaction through a fluted funnel reduces the forces required to compact the device and also eases further compaction of the device in accordance with the present invention.

The capture tube 50 for use with the present invention should have a number of preferred properties. First, the tube should be formed from a material that is both stiff and strong enough to fully contain an indwelling self-expanding implantable device without at any time becoming deformed by the expansive forces of the device. Second, in order to undergo the further compaction of the tube and indwelling device in the swaging step of the present invention, the tube should be formed from a material that will evenly compact from an inside diameter (ID) approximately equal to the intermediate profile 48 to an ID approximately equal to the fully compacted profile 34. The tube should undergo this transformation in ID without crimping or otherwise distorting the inner surface of the tube. Third, the tube should have a smooth inner surface so that the implantable device can be easily pulled into the tube during the initial pull down through the funnel. Fourth, the tube should continue to have a smooth inner surface following swaging so that the tube can be readily separated from the compacted implantable device at the appropriate time.

A suitable tube for use with the present invention may be formed from stainless steel, titanium, alloys, plastics or other suitable metals or polymers. Especially preferred for use with the present invention is work-hardenable stainless steel alloy. The tube dimensions will vary depending upon the implantable device that is being processed. For an endoprosthesis with the following dimensions about 5.8 mm outer diameter (OD)×about 50 mm. The tube is preferably dimensioned about 2.8 mm OD and about 2.5 mm ID and more preferably dimensioned about 2.08 mm OD and about 2.03 mm ID. The preferred tube for use with the present invention comprises a tube of Series 304 stainless steel available from Microgroup, Inc., of Medway, Mass., under part number 304H12XXTWX3.5 with 2.76 mm±0.02 mm OD and 2.54 mm±0.02 mm ID.

Once the implantable device 30 is contained in the capture tube 50, the capture tube 50 can then be further reduced in dimensions through a swaging process. "Swaging" as used in the present invention is intended to encompass any process by which the dimensions of the capture tube 50 can be further reduced. Swaging may be as simple as compressing the capture tube 50 by rolling it under pressure between a pair of plates, applying pressure to the tube by sequentially squeezing the tube using pliers or similar devices, or pulling the tube through a funnel-like device. Preferably, swaging is accomplished by using a machine that can apply an even compression to the tube along its entire length, such as by using a Rotary Swaging Machine available from Torrington Swager Vaill End Forming Machinery, Inc. of Torrington, Conn. under the designation No. 100. Swaging machines of this type use two or more swaging dies 52a, 52b, such as those shown in FIGS. 7 and 8. Alternatively, swaging can be provided using an iris-based crimping device, such as those commercially available from Machine Solutions, Inc., Flagstaff, Ariz., or similar compacting apparatus.

Figure 7:
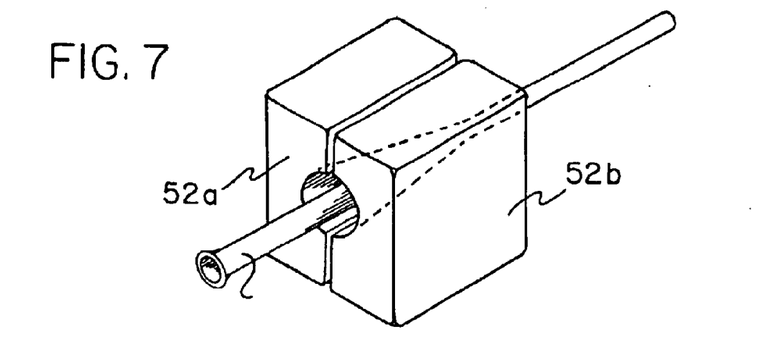
FIG. 7 is a schematic representation of a swaging die through which a capture tube and indwelling implantable device is compressed to a further reduced dimension.
Figure 8:
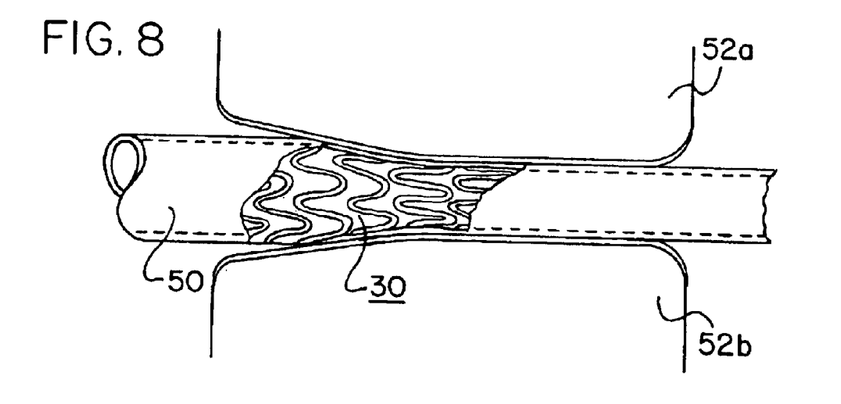
FIG. 8 is a cross section view of the capture tube and indwelling implantable device being compressed by the swaging die of FIG. 7, the implantable device being shown in partial cut-away through the capture tube.

As is illustrated in FIGS. 7 and 8, the capture tube 50 and indwelling implantable device 30 can be reduced from the intermediate profile 48 to the fully compacted profile 34 by passing the capture tube 50 through the swaging dies 52a, 52b while applying pressure to the dies.

Figure 9:
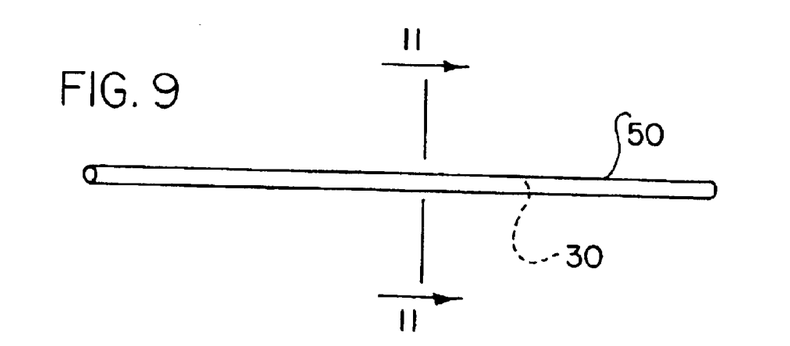
FIG. 9 is an isometric view of the capture tube having been compacted to a final cross sectional dimension with an indwelling implantable device.
Figure 10:
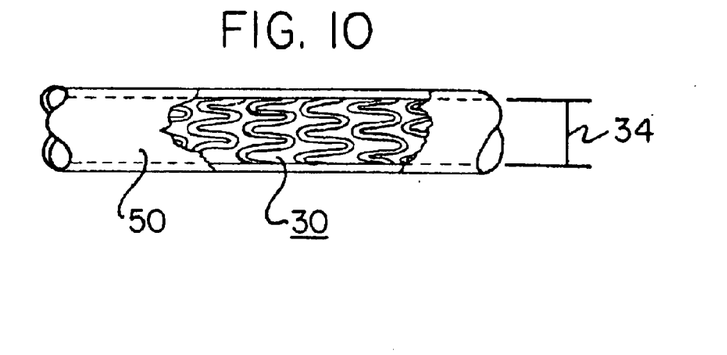
FIG. 10 is an enlarged sectional view of the capture tube of FIG. 9, showing the compacted implantable device in partial cut-away.
Figure 11:
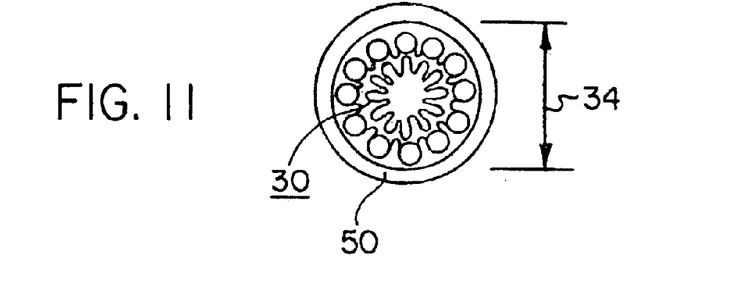
FIG. 11 is a cross-section view of the capture tube and device along line 11—11 of FIG. 9, showing the device at its final reduced dimension.
Figure 12:
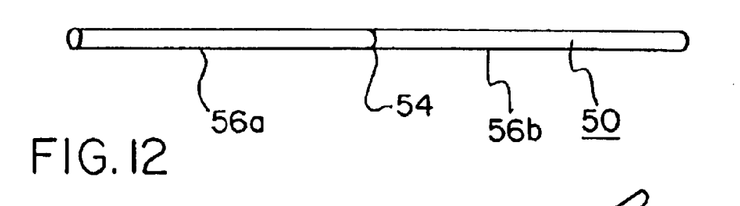
FIG. 12 is an isometric view of another embodiment of a capture tube of the present invention including a pre-determined break zone therein.
Figure 13:
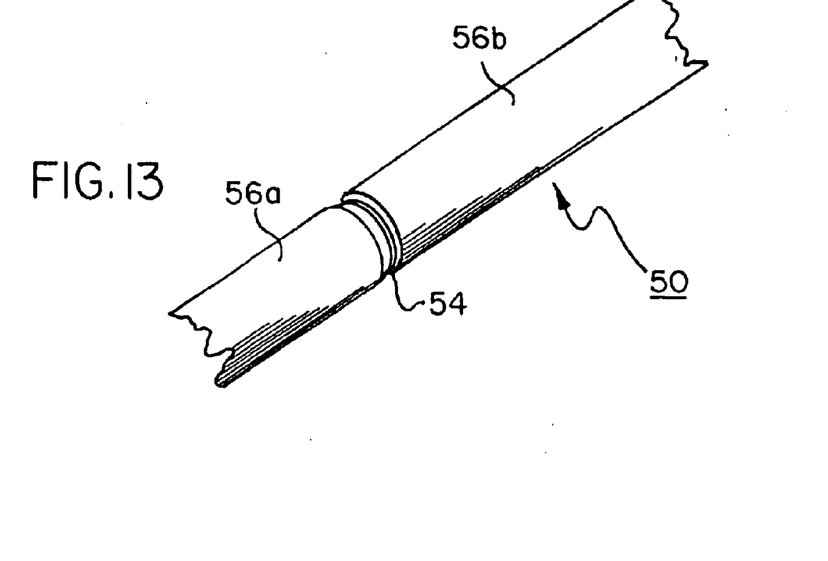
FIG. 13 is an enlarged partial isometric view of the capture tube of FIG. 12, showing the break zone.
Figure 14:
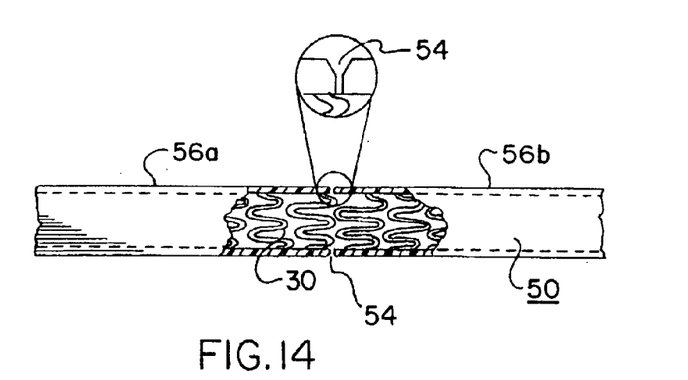
FIG. 14 is an enlarged side view of a capture tube having a break zone, showing in cut-away an indwelling implantable device and illustrating the break zone as a further enlarged insert.

Once the capture tube 50 is fully compressed, the tube is both compacted and may be extended in length, as is shown in FIG. 9. The indwelling implantable device 30 then assumes a tightly compressed fully compacted profile 34, as is shown in FIGS. 10 and 11.

Once the device is contained in the fully-compacted capture tube, the device can be packaged, sterilized, and maintained in the capture tube until the time of deployment, with the device being pushed out of the capture tube for ultimate deployment. Preferably, the device is alternatively transferred from the capture tube to other deployment apparatus for ultimate delivery to the patient. The deployment apparatus may comprise a flexible catheter that receives the compacted device from the capture tube by direct transfer of the compacted device by pushing the compacted device from the capture tube into the catheter. Alternatively, transfer can be accomplished by placing the capture tube within a catheter with an ID approximately equal to the outer diameter of the compacted capture tube and then pushing the compacted device out into the catheter for ultimate delivery. It should be evident that in this instance, the delivery profile of the implantable device will be slightly larger than the profile of the device as compacted in the capture tube.

The device may optionally be attached to and reside upon the delivery catheter while being subject to the entire swaging process.

The deployment apparatus may also comprise other deployment devices, such as sheaths or tubes of material that can contain the device in its compacted profile until the time of delivery and deployment. For example, the compacted device of the present invention can be transferred to the delivery apparatus taught in U.S. Pat. No. 5,352,561 to Leopold et al., or the delivery apparatus taught in U.S. Pat. No. 6,224,627 to Armstrong et al. A wide variety of other delivery apparatus that may be employed with the present invention, such as laced constraining and deploying apparatus (e.g., that disclosed in U.S. Pat. No. 5,919,225 to Lau et al.

A further improvement of the present invention is illustrated in FIGS. 12 through 16. In this embodiment, the capture tube 50 comprises one having at least one break zone 54 along its length. The break zone 54 may comprise any partition or weakening of the capture tube 50 at predetermined places along its length that facilitates separating the tube into two or more segments 56a, 56b. In the embodiment shown, the break zone 54 comprises a score line that allows the capture tube 50 to be cleanly and easily broken in half.

The break zone 54 should be strong enough to prevent the tube from twisting and breaking during swaging. After swaging, the break zone 54 should be weak enough to be readily broken in half. A suitable score line may be provided such as through machining or rolling. If appropriate materials are used, imparting work-hardening at the break zone during scoring and/or swaging may assist in the tube becoming very fragile in the scored area and aid in easy, clean, and consistent parting of the tube.

By using one or more break zones 54, the fully compacted device can be more easily transferred to delivery apparatus by separating the capture tube into segments 56a, 56b that each can be separately removed from the implantable device 30. As is explained in greater detail below, this allows the capture tube 50 to be removed with a fraction of the frictional force required to separate a non-segmented capture tube.

Figures 15, 16:
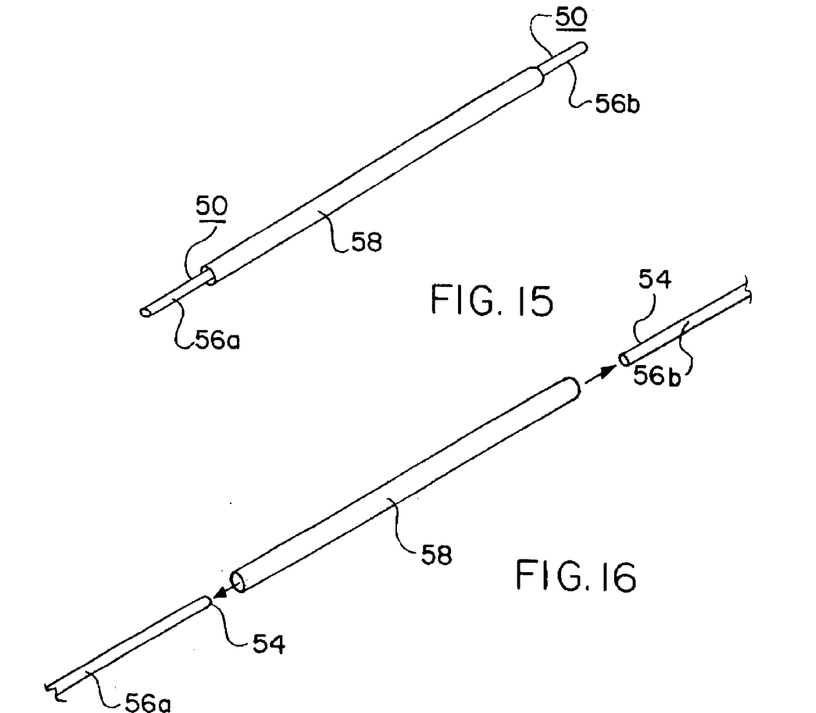
FIG. 15 is an isometric view of a capture tube having a break zone and an indwelling compressed implantable device, the capture tube having been compressed to have an outer diameter (OD) approximately equal to a final compacted dimension of the implantable device, and a delivery sheath positioned over the capture tube, the delivery sheath having an inner diameter (ID) approximately equal to the outer diameter of the compressed capture tube.
FIG. 16 is an isometric view of the capture tube and delivery sheath of FIG. 15, showing the capture tube having been separated at its break zone and each resulting half of the capture tube being removed from the sheath, leaving the implantable device contained at its final compacted dimension within the sheath.

FIG. 15 illustrates a fully compacted capture tube 50 having a break zone 54 provided therein placed within a delivery and deployment device 58, such as a catheter or deployment sleeve. Once properly positioned within the deployment device 58, the capture tube 50 can be separated at the break zone 54 and each of the segments 56a, 56b can be separately removed, as is shown in FIG. 16.

Alternative break zones 54 for use with the present invention may include: chemical etched areas, heat treating of selected areas of the tube, perforations (e.g., drilled, chemical mill, etched, or laser perforations), mechanical removal of tube material, or combinations thereof.

Alternative means for transferring the fully compacted implantable device of the present invention into delivery apparatus may also include: pulling the device from the capture tube into the delivery apparatus (for instance, by leaving the tethers attached or reattaching tether lines for the transfer, otherwise actuating mechanically, or actuating pneumatically (i.e., by using a vacuum)); pushing the device from the capture tube into the delivery apparatus (for instance, through mechanical, pneumatic, and/or hydraulic means); or combinations of both pushing and pulling. If the device is reduced and swaged on a delivery catheter, transfer can be accomplished by pulling and/or pushing the delivery catheter.

Figure 17:
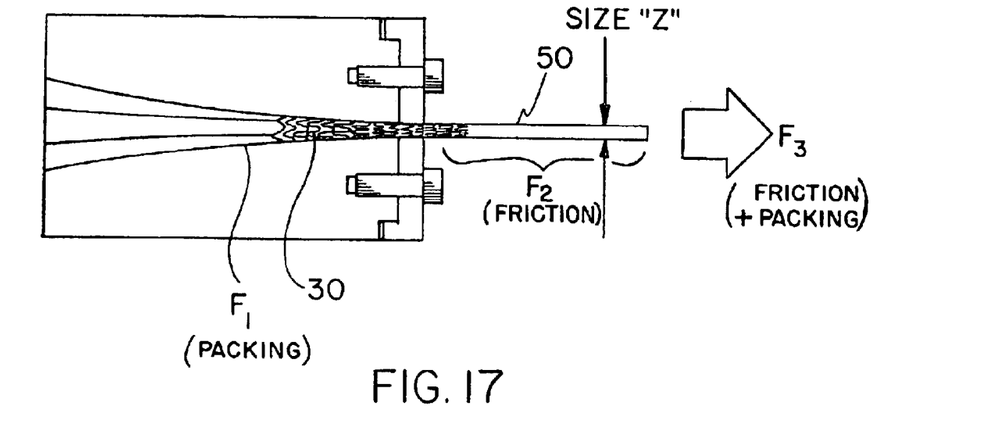
FIG. 17 is a side cross section view of an implantable device of the prior art being compacted through a funnel from an initial dimension to a final delivery dimension within a delivery tube having a dimension of "Z" and the forces $F_1$ and $F_2$ (resulting in overall force $F_3$) encountered in such compaction.
Figure 18:
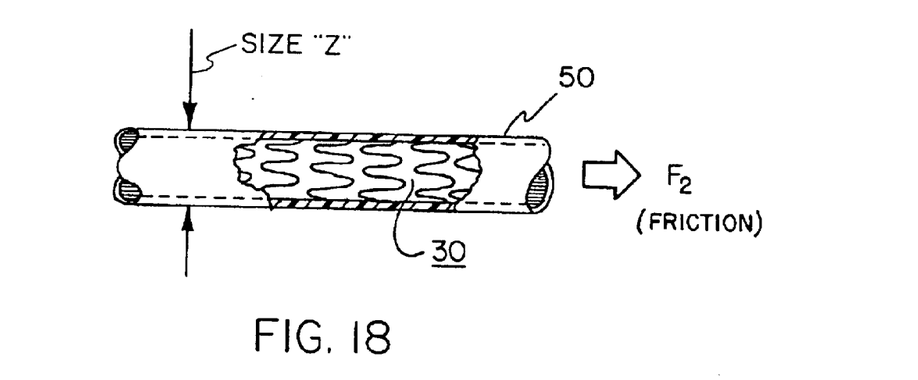
FIG. 18 is a side partial cut-away view of the implantable device and delivery tube of FIG. 17 showing force $F_2$ encountered in deploying the device from the delivery tube.

FIGS. 17 and 18 illustrate the interaction of forces acting upon a self-expanding stent-graft during diametrical compaction and loading in a conventional loading process. FIGS. 19 through 24 illustrate the forces acting upon a self-expanding stent-graft when loaded in accordance with the present invention. With respect to all of FIGS. 17 through 24, the following convention is applied:

$F_1$ is the force required to radially compact the device;

$F_2$ is the friction encountered within the capture tube;

$F_3$ is the sum of $F_1$ and $F_2$

In FIG. 17, a stent-graft 30 is depicted undergoing a conventional compaction and loading process in which the device is reduced in one step to the required introductory size of "Z." In this process, $F_1$ and $F_2$ are combined and result in $F_3$. If $F_3$ is greater than the tensile break force of the stent-graft 30, the device will tear during the compacting process. Typically, minimally invasive devices tend to be relatively delicate. Conversely, if one were to make a device more robust, the mass would likely increase, which would further complicate the compaction process and negatively impact ultimate delivery profiles. FIG. 18 shows the stent-graft 30 fully compacted within a capture tube 50. To withdraw the stent-graft 30 from the capture tube 50 in this configuration will require a force equal to or greater than $F_2$.

Figure 19:
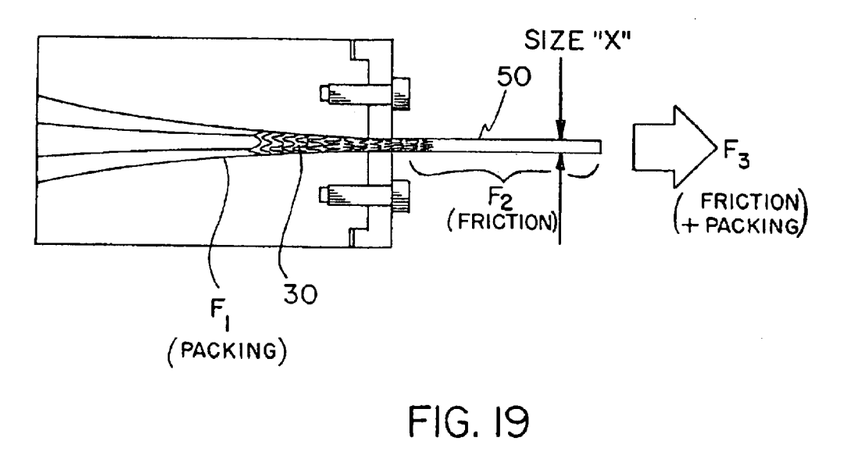
FIG. 19 is a side cross section view of an implantable device of the present invention being compacted through a funnel from an initial dimension to an intermediate dimension within a capture tube having a dimension of "X" and the forces $F_1'$ and $F_2'$ (resulting in overall force $F_3'$) encountered in such compaction.
Figure 20:
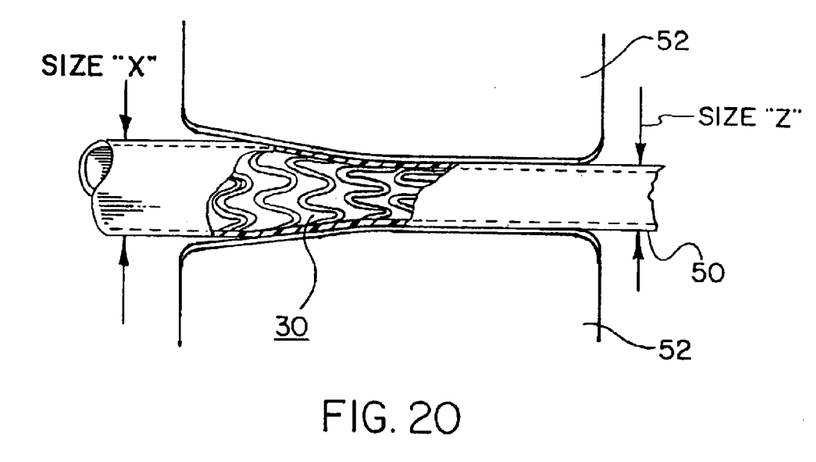
FIG. 20 is a side cross section view of an implantable device and capture tube of FIG. 19 being further compacted from dimension "X" to final dimension "Z" in a swaging die.
Figure 21:
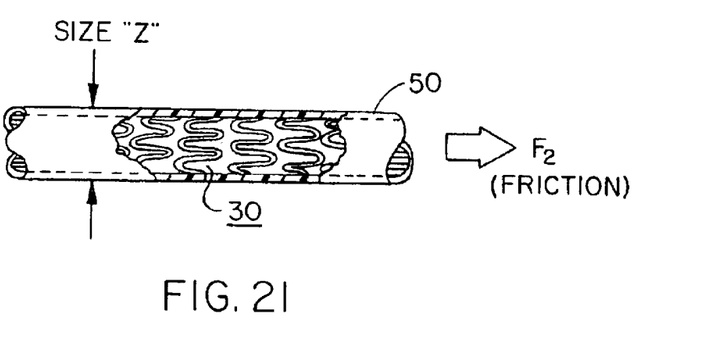
FIG. 21 is a side partial cut-away view of the implantable device and capture tube of FIG. 20 showing force $F_2$ encountered in deploying the device from the capture tube.

In FIG. 19, the same size stent-graft 30 is depicted undergoing a compaction and loading process in which the device is reduced to an intermediate diameter of size "X". In this case the force required is also a sum of two forces $F_1'$ and $F_2'$, but this sum is a much lesser value than in conventional compaction process of FIG. 17, since the work required to pack the device at the intermediate size "X" is less and the friction in the deformable capture tube 50 is less. Once loaded into the deformable capture tube 50 at intermediate size "X", as is shown in FIG. 20, the tube 50 and device 30 are compacted further to introductory size "Z" in a swaging machine 52. At introductory size "Z," as illustrated in FIG. 21, the force required to withdraw the stent-graft 30 will be $F_2$ (the same as the force required to withdraw from the capture tube 50 illustrated in FIG. 18). As a result, an identical stent-graft 30 can be reduced to an identical profile in the process of FIGS. 19 through 21 with less longitudinal force applied to the device in the compaction process (that is, a force of $F_3'$ instead of $F_3$, wherein $F_3'<F_3$). This significant reduction in overall required compaction force achieved by the present invention is the result of the "de-coupling" of the compaction force $F_1'$ and the capture tube frictional force $F_2'$ from the full force required to achieve a fully compacted profile "Z."

It has been determined that the de-coupling of these forces allows the present invention to compact identical medical devices to smaller delivery profiles than were previously possible by funnel reduction methods alone (that is, previously devices would tear apart before reaching the small profiles possible with the present invention). Additionally, since the longitudinal strength of the devices is less of an issue in the compaction process, the de-coupling of these forces may allow devices to contain less mass than previous devices so that even smaller delivery profiles are now achievable.

Figure 22:
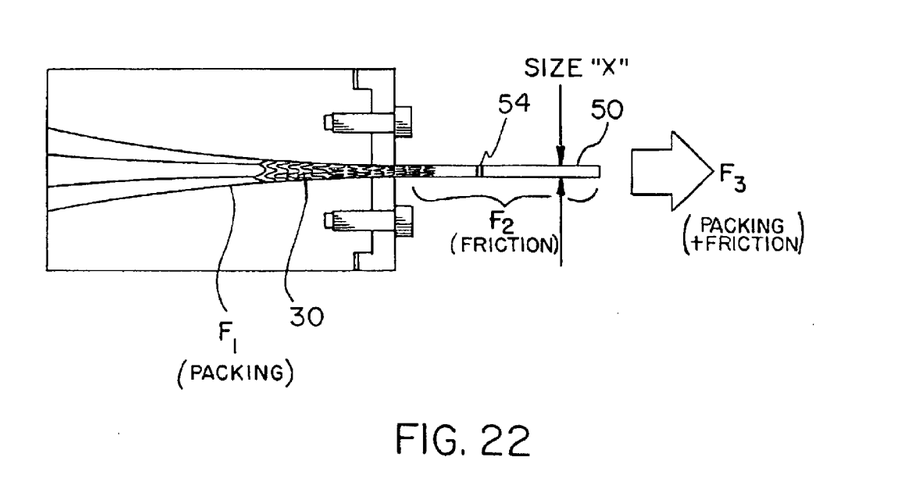
FIG. 22 is a side cross section view of an implantable device of the present invention being compacted through a funnel from an initial dimension to an intermediate dimension within a capture tube (including a break zone), having a dimension of "X" and the forces $F_1'$ and $F_2'$ (resulting in overall force $F_3'$) encountered in such compaction.
Figure 23:
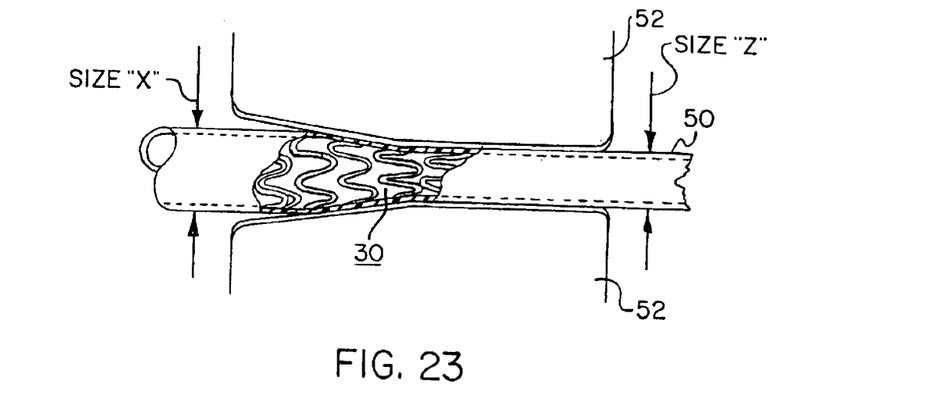
FIG. 23 is a side cross section view of an implantable device and capture tube of FIG. 22 being further compacted from dimension "X" to final dimension "Z" in a swaging die.
Figure 24:
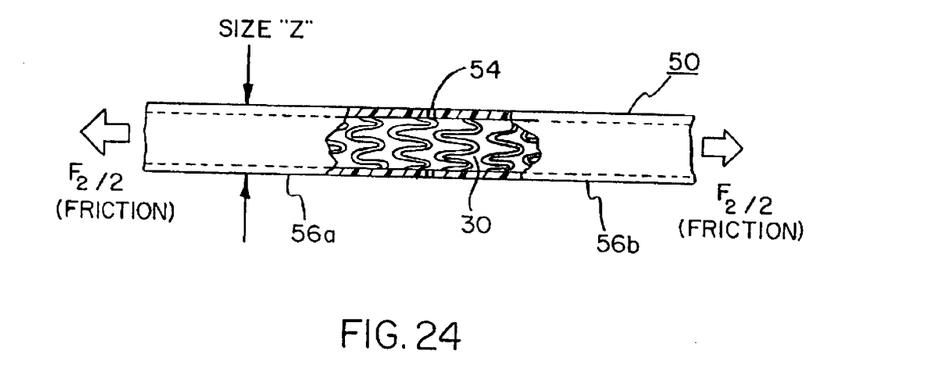
FIG. 24 is a side partial cut-away view of the implantable device and capture tube of FIG. 23 showing forces 1/2 $F_2$ encountered in deploying the device from the capture tube that is separated at the break zone.

FIGS. 22 and 23 depict a stent-graft 30 undergoing the same process illustrated in FIGS. 19 and 20 except that a deformable capture tube 50 is used having a break zone 54 provide therein. As is illustrated in FIG. 24, a further significant force reduction is achieved by parting the deformable capture tube 50 after swaging and pulling each half off either end. In effect, this divides force $F_2$ by a factor of approximately 2 (that is, since each segment 56a, 56b is one-half the overall length of tube 50, each segment will require approximately one-half the frictional force in order to separate each of the segments from the device 30). Thus, the use of a capture tube with one or more break zones therein can further reduce the frictional forces that the device will encounter during the device preparation process and again can allow devices to be used that have less mass than was previously possible.

Figure 25:
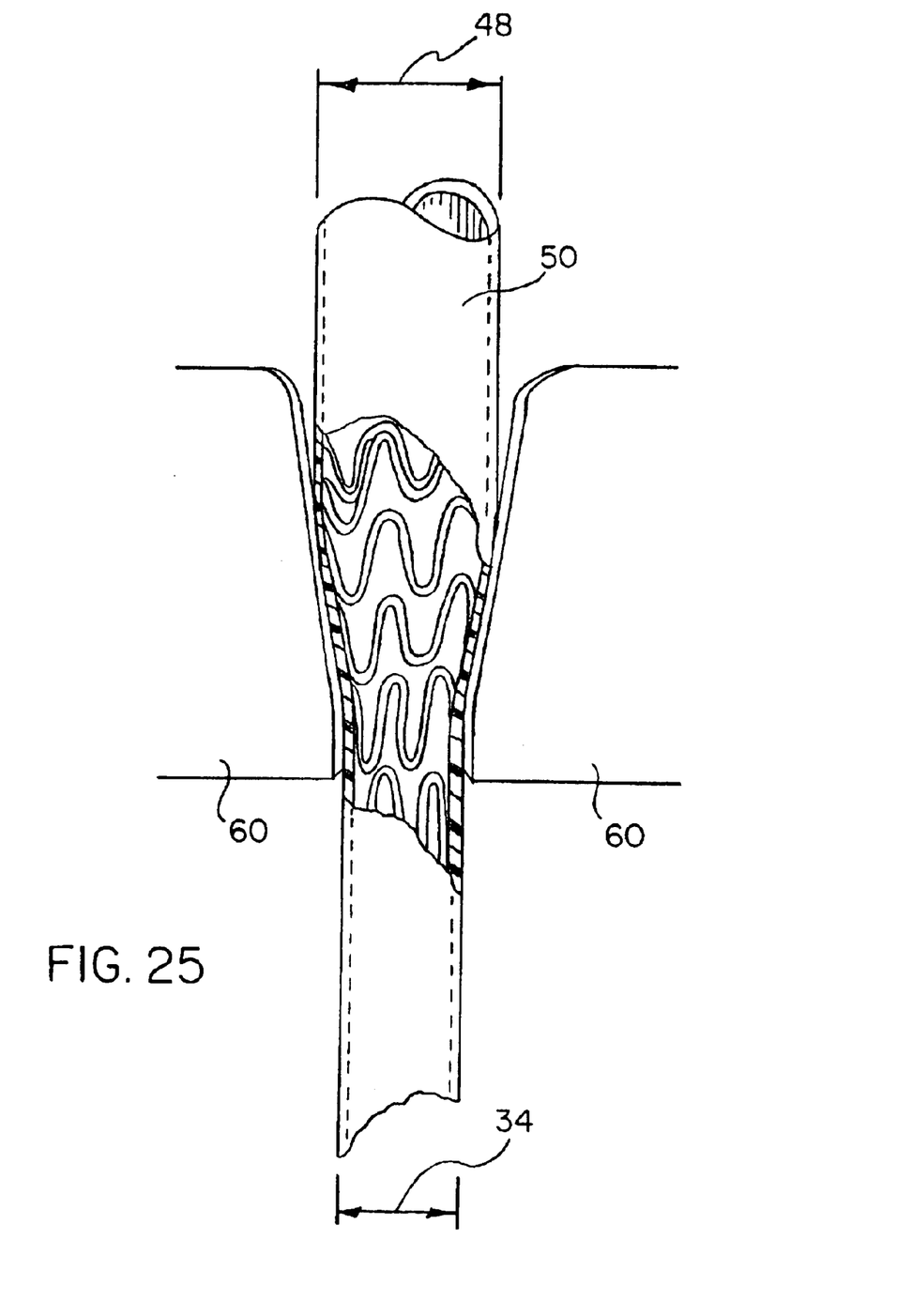
FIG. 25 is an enlarged cross section view of an alternative swaging tapered die for use in the present invention, showing a capture tube and, in cut-away, a indwelling implantable device.

FIG. 25 illustrates an alternative swaging device for use with the present invention. In this instance, swaging is accomplished by drawing, pushing, or otherwise actuating the capture tube 50 through a reduction die 60, such as a funnel. The reduction die 60 should be constructed to allow the capture tube 50 to easily pass through it and provide a smooth transition from the intermediate profile to the fully compacted profile. A reduction die is preferably constructed from hardened tool steel (e.g., D2 or A2 tool steel) or carbide, and may include a friction-reducing surface, such as PTFE and/or an applied lubricant. Further alternative means for swaging the capture tube 50 in accordance with the present invention may include compacting the device within a chuck, collet, iris, and/or tapered die device, and perhaps repeating such compacting to achieve the desired compacted configuration along the length of the capture tube.

Figure 26:
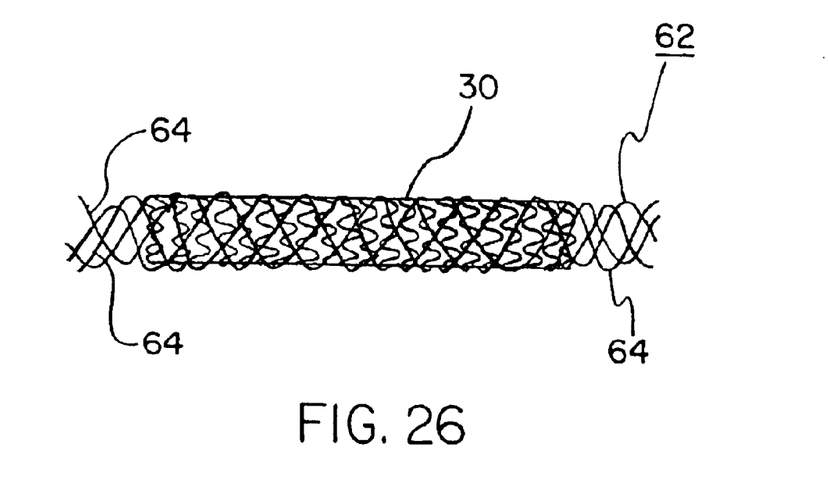
FIG. 26 is a side view of an alternative compaction method of the present invention comprising an implantable medical device contained in a braided compaction tube.
Figure 27:
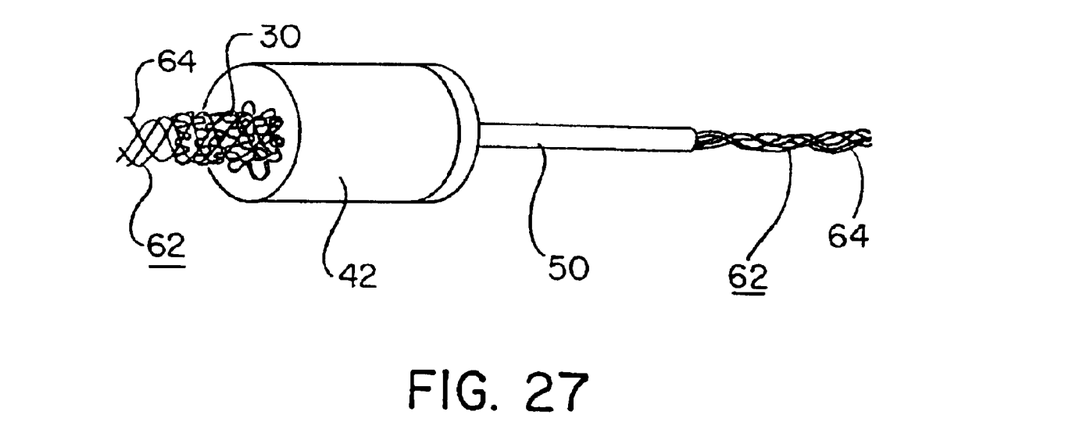
FIG. 27 is an isometric view of the implantable device and braided compaction tube of FIG. 26 being drawn through a funnel into a capture tube.

FIGS. 26 and 27 show an alternative compaction method of the present invention. In this instance, a braided tube 62 is employed to surround the implantable device 30 and aid in actuating the device through a fluted funnel 42 into capture tube 50. The braided filaments 64 act as a "finger trap" to grip the entire implantable device 30 equally along its length during the draw down process. This gripping by the braid obviates the need to attach draw strings to the stent-graft itself, thus preventing damage to the stent-graft and eliminating a time consuming tether line attachment step in the process. The stent-graft is drawn through the die (by use of braided filament tube) and into a deformable capture tube 50, as previously described. Once the device 30 is positioned within the capture tube 50, the braided tube 62 can be removed by pulling out the filaments 64 one or more at a time.

The braided capture tube may be constructed from a wide variety of materials, including PTFE filaments, ePTFE filaments, nylon, KEVLAR® polyamide, metal filaments, or the like. The preferred braided capture tube comprises a polymer or metal filament with about 0.1 mm OD and having a braided construction comprising about 8 filaments braided in a one-over-one-under configuration, with about 20 to 25 picks per inch.

Without intending to limit the scope of the present invention, the following examples illustrate how the present invention may be made and used.

EXAMPLE 1

One embodiment of the present invention employing tether lines may be practiced in the following manner.

I. Initial Profile Reduction Using Tether Lines

1. Using a Singer sewing needle and 200 denier RAS-TEX® PTFE fiber available from W.L. Gore and Associates, Inc., Elkton, Md., thread three 18 inch long tether lines through alternate end apexes on one end of a VIABAHN™ endoprothesis available from W.L. Gore & Associates, Inc., Flagstaff, Ariz.;

2. Evenly tension the three tether lines and tie together with a common knot, as shown in FIG. 1;

3. Form a work hardened circumferential score line approximately at the middle of a 304 stainless steel hypotube (2.76 mm±0.02 mm OD, 2.54 mm±0.02 ID) available from Microgroup, Medway Mass.;

3. Thread and draw the tether lines with attached endoprothesis through fluted funnel, as shown in FIGS. 3 and 4, into the hypotube attached to the end of the funnel;

4. Align the approximate midpoint of the endoprothesis at the circumferential score line;

5. Remove the hypotube from the funnel by removing funnel cap;

6. Cut and remove the tether lines from the captured endoprothesis. The endoprosthesis is now captured within the hypotube at an intermediate profile.

II. Radial Compression

1. Employing a rotary swager with swage dies about 2.15 mm (Model 100 from Torrington Swager and Vaill End Forming Machinery Inc, Waterbury, Conn.), feed the stainless steel hypotube and indwelling endoprosthesis into the swager. Swage the hypotube until at least half of it is completely reduced to a final profile;
2. Withdraw the hypotube from the swager while it continues to run;
3. Feed the opposite end of the hypotube into the swager until hypotube and indwelling endoprosthesis are completely reduced to the final profile;
4. Wipe down the outside of reduced hypotube, with endoprothesis inside, using 70% IPA.

III. Transfer to Delivery Apparatus
1. A break away constraint (BAC) delivery sleeve, such as that taught in U.S. Pat. No. 5,352,561 to Leopold et al., is mounted over the reduced hypotube until leading edge of the BAC is even with the worked hardened circumferential scored line;
2. The reduced hypotube is broken at the scored line;
3. Continue loading BAC over reduced hypotube until midpoint of the BAC is located over the broken scored line;
4. Separate the reduced hypotube at broken scored line capturing the endoprothesis in the BAC;
5. Ensure that the endoprothesis is entirely captured by and properly centered in the BAC.

EXAMPLE 2

A second embodiment of the present invention may be constructed in the following manner.

I. Initial Profile Reduction Using Braid
1. Cut approximately a four-inch segment of nylon eight-filament braid from a construction core, such as that available from ViaMed Corporation, South Easton, Mass., with a construction of one over, one under diamond pattern, 25 picks/inch;
2. Axially compress the braid segment and load over a VIABAHN™ endoprothesis by sliding compressed braid segment onto endoprothesis. Pull light tension on braid. The endoprothesis should be off-centered within the braid length;
3. Applying tension, draw the endoprothesis through the fluted funnel shown in FIGS. 3 and 4 into a 2.76 mm±0.02 mm OD, 2.54 mm±0.02 ID 304 stainless steel hypotube that includes a circumferential score line. The hypotube should be mounted on the end of the funnel;
4. Locate the midpoint of the endoprothesis at the circumferential score line in the middle of the hypotube;
5. Remove the hypotube from the funnel by removing the funnel cap.
6. Remove each filament of braid one at a time by hand until all the filaments have been removed.

II. Transfer to Delivery Apparatus
1. Employing a rotary swager with swage dies about 2.15 mm (Model 100 from Torrington Swager and Vaill End Forming Machinery Inc, Waterbury, Conn.), feed the stainless steel hypotube and indwelling endoprosthesis into the swager. Swage the hypotube until at least half of it is completely reduced to a final profile;
2. Withdraw the hypotube from the swager while it continues to run;
3. Feed the opposite end of the hypotube into the swager until hypotube and indwelling endoprothesis are completely reduced to the final profile;
4. Wipe down the outside of reduced hypotube, with endoprothesis inside, using 70% IPA.

III. Transfer to Delivery Apparatus
1. A break away constraint (BAC) delivery sleeve, such as that taught in U.S. Pat. No. 5,352,561 to Leopold et al., is mounted over the reduced hypotube until leading edge of the BAC is even with the worked hardened circumferential scored line;
2. The reduced hypotube is broken at the scored line;
3. Continue loading BAC over reduced hypotube until midpoint of the BAC is located over the broken scored line;
4. Separate the reduced hypotube at broken scored line capturing the endoprothesis in the BAC;
5. Ensure that the endoprothesis is entirely captured by and properly centered in the BAC.

EXAMPLE 3

A third embodiment of the present invention may be practiced in the following manner.

I. Initial Profile Reduction Using Tether Lines
1. Using a Singer sewing needle and 200 denier RASTEX® PTFE fiber available from W.L. Gore and Associates, Inc., Elkton, Md., thread three 18 inch long tether lines through alternate end apexes on one end of a VIABAHN™ endoprothesis available from W.L. Gore & Associates, Inc., Flagstaff, Ariz.;
2. Evenly tension the three tether lines and tie together with a common knot, as shown in FIG. 1;
3. Form a work hardened circumferential score line approximately at the middle of a 304 stainless steel hypotube (2.76 mm±0.02 mm OD, 2.54 mm±0.02 ID) available from Microgroup, Medway Mass.;
4. Thread and draw the tether lines with attached endoprothesis through fluted funnel, as shown in FIGS. 3 and 4, into the hypotube attached to the end of the funnel;
4. Align the approximate midpoint of the endoprothesis at the circumferential score line;
5. Remove the hypotube from the funnel by removing funnel cap;
6. Cut and remove the tether lines from the captured endoprothesis. The endoprosthesis is now captured within the hypotube at an intermediate profile.

II. Flat Die Reduction of Hypotube
1. Crimp 12.7 mm of one end of the hypotube. Ensure not to crimp the indwelling endoprothesis;
2. Place a "Tuning Fork" flat die holder, made by KPG Machine, Danielson, Conn., into the bottom jaws of a Model #5564 INSTRON tensile tester, available from Instron Corp., Canton, Mass.;
3. Use a fully hardened D2 tool steel 12.7 mm×12.7 mm×3.175 mm flat tapered die with a 2.15 mm reducing tapered hole bore out at its center, also available from KPG Machine. Place the tapered die into holder, with the larger diameter of the tapered hole facing down;
4. Fit the crimped end of the hypotube through the larger diameter of the tapered hole of the flat tapered die;
5. Close the top jaws of INSTRON tensile tester onto the 3.175 mm crimped portion of hypotube;
6. Press the "UP" button on the tensile tester to begin drawing the 304 stainless steel hypotube through the flat tapered die. The drawing process is complete when the hypotube is completely reduced;
7. Open the top jaw and remove the hypotube;

8. Wipe down the outside of reduced hypotube, with endoprothesis inside, using 70% IPA.

III. Transfer to Delivery Apparatus

1. A break away constraint (BAC) delivery sleeve, such as that taught in U.S. Pat. No. 5,352,561 to Leopold et al., is mounted over the reduced hypotube until leading edge of the BAC is even with the worked hardened circumferential scored line;
2. The reduced hypotube is broken at the scored line;
3. Continue loading BAC over reduced hypotube until midpoint of the BAC is located over the broken scored line;
4. Separate the reduced hypotube at broken scored line capturing the endoprothesis in the BAC;
5. Ensure that the endoprothesis is entirely captured by and properly centered in the BAC.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method of reducing the cross sectional dimension of a medical device comprising:

providing a medical device having an initial cross sectional profile;

providing a restraining member;

reducing the initial cross sectional profile of the medical device to an intermediate cross sectional profile;

placing the medical device at its intermediate cross sectional profile into the restraining member;

applying radial compressive forces to the restraining member to further reduce the cross sectional profile of the medical device.

2. The method of claim 1 that further comprises reducing the initial cross sectional profile of the medical device by passing it through a funnel.

3. The method of claim 1 that further comprises reducing the initial cross sectional profile of the medical device by applying a radial compressive force.

4. The method of claim 1 that further comprises removing the medical device from the restraining member following application of the radial compressive force.

5. The method of claim 1 that further comprises providing a restraining member that is a tube.

6. The method of claim 1 that further comprises providing a restraining member that is removed prior to introduction of the medical device into a patient.

7. The method of claim 6 that further comprises placing the compressed medical device into a constraint following removal from the restraining member.

8. The method of claim 1 that further comprises providing a restraining member that is a braided tube.

9. The method of claim 8 that further comprises providing a braided tube comprising multiple filaments, wherein each of the filaments is removed following further reduction of the cross sectional profile of the device.

10. The method of claim 1 that further comprises providing a medical device that is self-expanding.

11. The method of claim 10 that further comprises providing a self-expanding medical device that comprises a stent.

12. A method of reducing the cross sectional dimension of a medical device comprising:

providing a medical device having an initial cross sectional profile;

providing a capture tube;

reducing the initial cross sectional profile of the medical device to an intermediate cross sectional profile;

placing the medical device at its intermediate cross sectional profile into the capture tube;

applying radial compressive forces to the restraining member to further reduce the cross sectional profile of the medical device;

transferring the medical device at its further reduced cross sectional profile from the capture tube to delivery apparatus.

13. The method of claim 12 that further comprises providing a medical device that is self-expanding.

14. The method of claim 13 that further comprises providing a self-expanding medical device that comprises a stent.

15. The method of claim 12 that further comprises providing a capture tube that comprises a tube of continuous material.

16. The method of claim 12 that further comprises providing a capture tube that comprises a tube of braided material.

* * * * *